United States Patent
Frankel et al.

(10) Patent No.: US 10,786,283 B2
(45) Date of Patent: Sep. 29, 2020

(54) SKELETAL BONE FIXATION MECHANISM

(71) Applicant: MUSC Foundation for Research Development, Charleston, SC (US)

(72) Inventors: Bruce M. Frankel, Mount Pleasant, SC (US); Mark Evald Semler, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 483 days.

(21) Appl. No.: 13/957,190

(22) Filed: Aug. 1, 2013

(65) Prior Publication Data

US 2015/0039034 A1    Feb. 5, 2015

(51) Int. Cl.
*A61B 17/70* (2006.01)
*A61B 90/00* (2016.01)

(52) U.S. Cl.
CPC ...... *A61B 17/7011* (2013.01); *A61B 17/7013* (2013.01); *A61B 17/7032* (2013.01); *A61B 90/06* (2016.02); *A61B 17/7085* (2013.01); *A61B 2090/037* (2016.02); *A61B 2090/066* (2016.02)

(58) Field of Classification Search
CPC ............ A61B 17/7011; A61B 17/7013; A61B 17/70–7041; A61B 17/7074–7091
USPC ....................................... 606/86 A, 104, 914
See application file for complete search history.

(56) References Cited

U.S. PATENT DOCUMENTS

| | | | |
|---|---|---|---|
| 6,355,039 B1 | 3/2002 | Troussel et al. | |
| 6,379,358 B1 | 4/2002 | Kuo | |
| 7,678,139 B2 | 3/2010 | Garamszegi et al. | |
| 7,976,546 B2* | 7/2011 | Geist et al. | 606/86 A |
| 8,075,592 B2 | 12/2011 | Landry et al. | |
| 8,216,282 B2 | 10/2012 | Hua | |
| 8,454,664 B2 | 6/2013 | McLean | |
| 8,500,741 B2* | 8/2013 | Hansen | A61B 17/7074 606/103 |
| 8,540,719 B2* | 9/2013 | Peukert | A61B 17/708 606/103 |
| 2006/0064092 A1 | 3/2006 | Howland | |
| 2006/0184171 A1* | 8/2006 | Biedermann et al. | 606/61 |
| 2006/0229608 A1 | 10/2006 | Foster et al. | |
| 2007/0233079 A1* | 10/2007 | Fallin et al. | 606/61 |
| 2007/0288008 A1 | 12/2007 | Park | |
| 2008/0082103 A1* | 4/2008 | Hutton et al. | 606/73 |

(Continued)

*Primary Examiner* — Ellen C Hammond
(74) *Attorney, Agent, or Firm* — Riverside Law LLP

(57) ABSTRACT

A skeletal fixation apparatus may include two or more bodies that are attached to two or more screws that have been inserted into vertebral bodies associated with a patient. The apparatus may also include two or more cylindrical members that are attached to the bodies to control the movement or alignment of the bodies when the skeletal fixation apparatus is being installed in the patient. The apparatus may further include a rod that includes a first curvature and a second curvature. The first curvature may be different than the second curvature and may be based on a medical diagnosis associated with stabilizing the vertebral bodies. The second curvature may enable the bodies to be immovably fastened to the rod in a manner that precludes the cylindrical members from contacting each other or causing a false torque condition to exist when the skeletal fixation apparatus is installed in the patient.

18 Claims, 10 Drawing Sheets

(56) References Cited

U.S. PATENT DOCUMENTS

| | | |
|---|---|---|
| 2008/0177318 A1* | 7/2008 | Veldman et al. ............. 606/256 |
| 2008/0262552 A1* | 10/2008 | Kim ............................ 606/276 |
| 2009/0099605 A1 | 4/2009 | Fallin et al. |
| 2009/0228052 A1* | 9/2009 | Beardsley .......... A61B 17/7032 |
| | | 606/305 |
| 2009/0254326 A1* | 10/2009 | Isaacs ............................ 703/11 |
| 2010/0036425 A1* | 2/2010 | Barrus et al. ................. 606/264 |
| 2010/0111631 A1 | 5/2010 | Trieu et al. |
| 2011/0004249 A1 | 1/2011 | Wu et al. |
| 2011/0071570 A1* | 3/2011 | Trieu ........................... 606/254 |
| 2011/0087293 A1* | 4/2011 | Ferreira ............ A61B 17/7088 |
| | | 606/265 |
| 2011/0172714 A1 | 7/2011 | Boachie-Adjei et al. |
| 2011/0196426 A1* | 8/2011 | Peukert .............. A61B 17/7083 |
| | | 606/279 |
| 2011/0202095 A1 | 8/2011 | Semler et al. |
| 2012/0065687 A1* | 3/2012 | Ballard et al. ................ 606/259 |
| 2013/0035728 A1 | 2/2013 | Jackson |
| 2015/0073482 A1* | 3/2015 | Ludwig et al. ............... 606/266 |

* cited by examiner

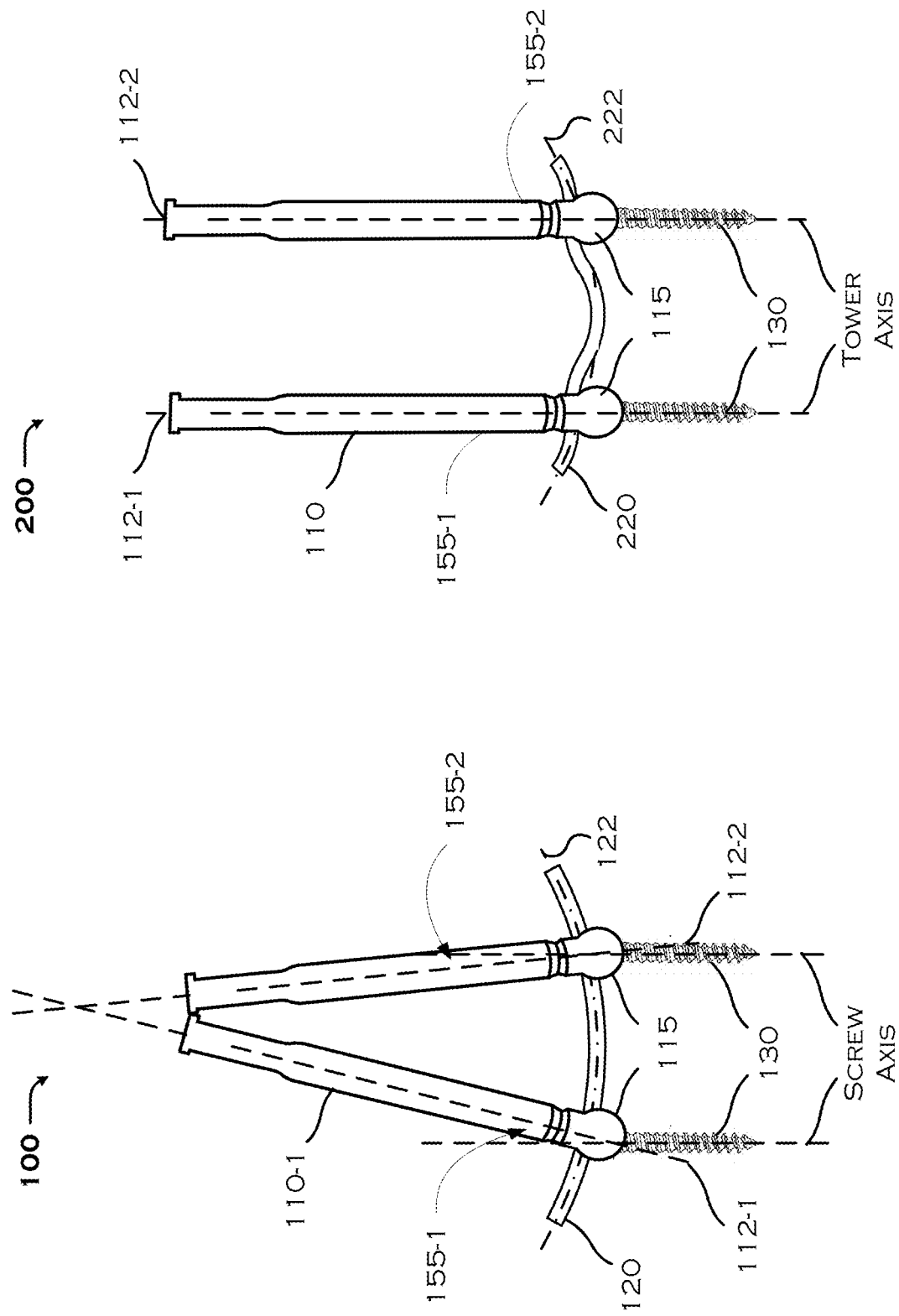

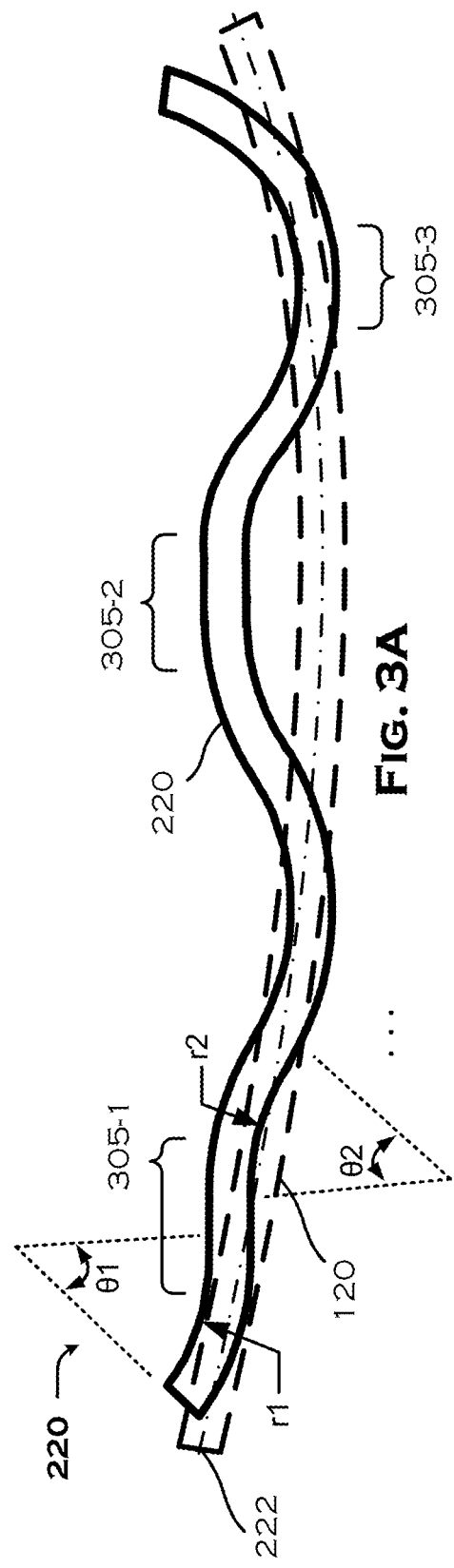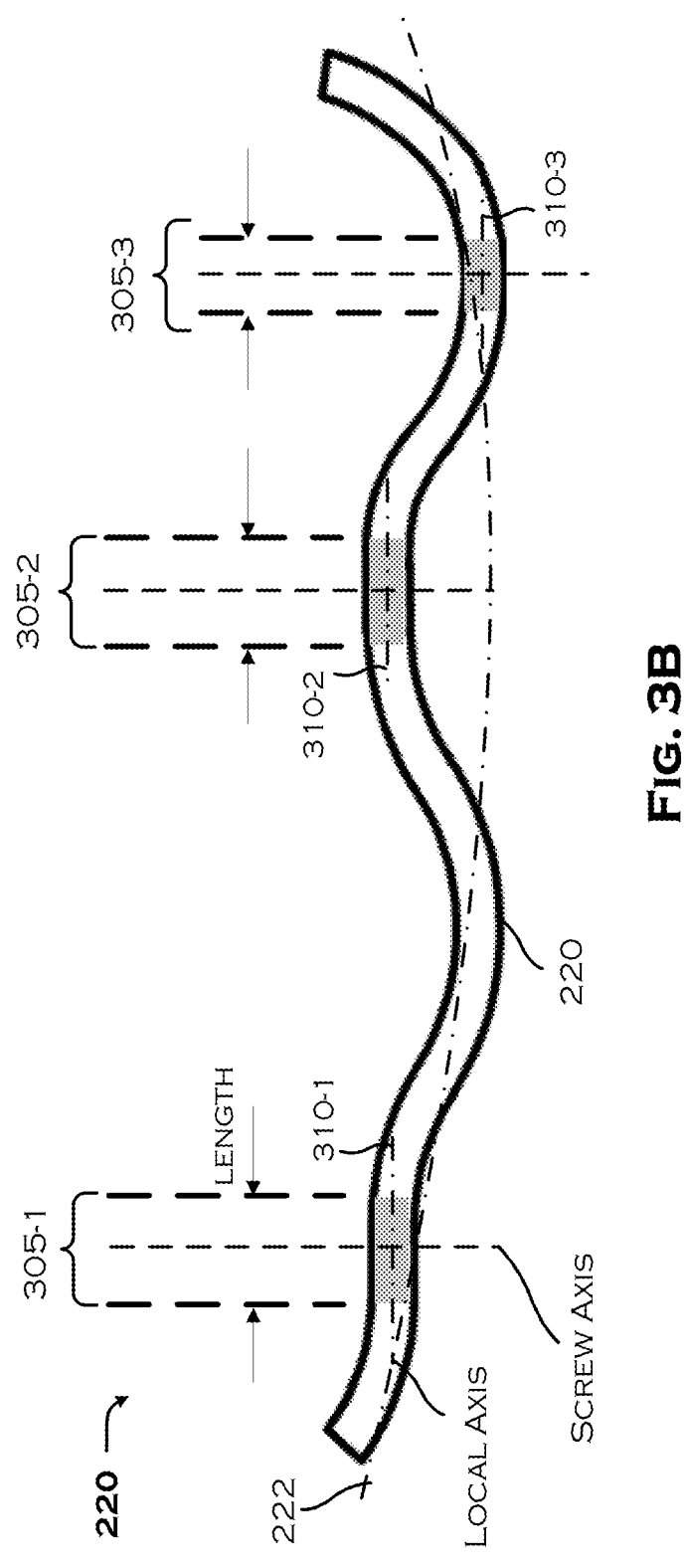
FIG. 3A
FIG. 3B

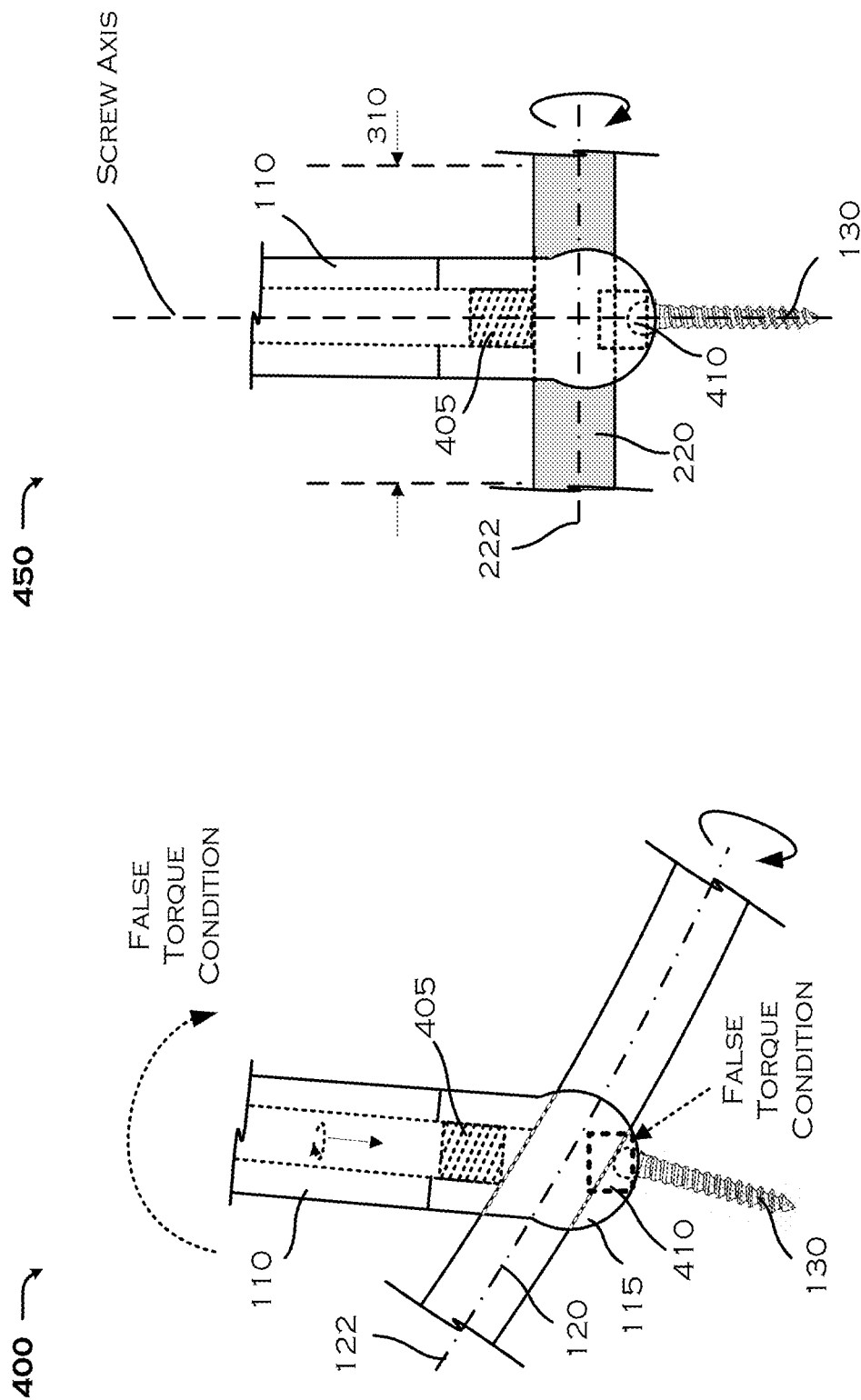

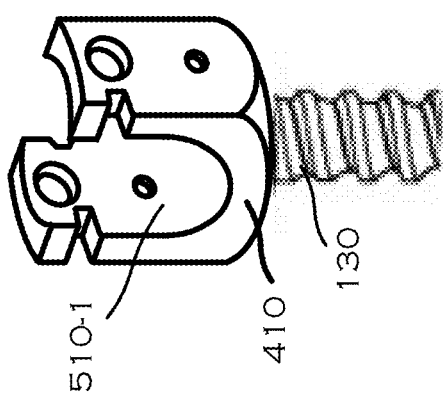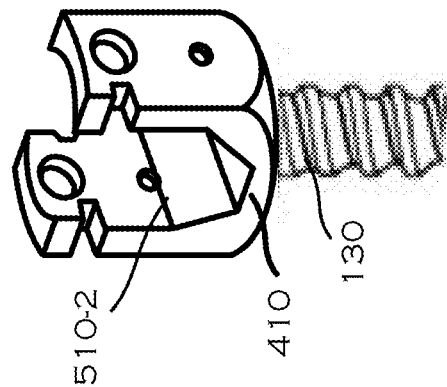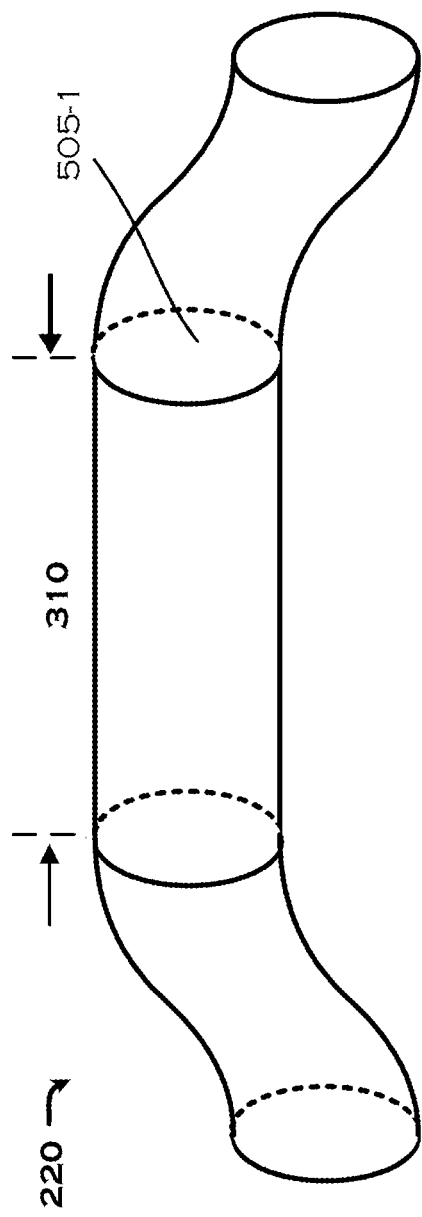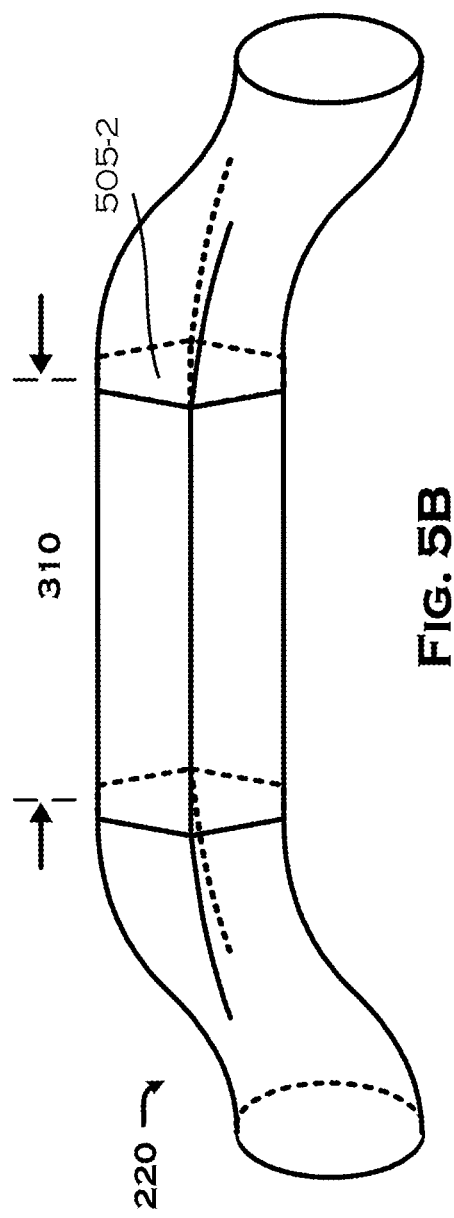
FIG. 5A
FIG. 5B

US 10,786,283 B2

SKELETAL BONE FIXATION MECHANISM

BACKGROUND

Procedures associated with posterior minimally invasive lumbar spinal fusion often use extended tab screws (e.g., pedicle screws), screw extension towers, and a rigid fixation rod (e.g., to which the screw extension towers are immovably fastened) (hereinafter, a "skeletal fixation assembly") to fixate vertebral bodies to one another. Fixating the vertebral bodies precludes or reduces a degree to which the vertebral bodies can change position and/or orientation relative to each other or relative to another portion of a spinal column of a patient; thus enabling a portion of a spine to which skeletal fixation assembly is attached to be stabilized.

In the highly lordotic areas of the cervical and lumbosacral areas of the spinal column, bend radii or arc of the fixation rod can cause two or more screw extension towers to come into contact and/or interfere with each other. When such interference occurs, the certain induced loads (e.g., a compressive force, a torque, a tension force, a stress, a strain, a sheering force, etc.) may be imparted to the fixation rod and/or pedicle screw when a body of an extended screw (to which a screw extension tower is removably attached) is fastened to the fixation rod (hereinafter referred to as "false torque" or "a false torque condition"). Additionally, a false torque condition may exist in regions of exaggerated sagittal imbalance and kyphotic curves in the cervico-thoracic, and thoracic spine or other regions with coronal plane deformities. When the extension towers are removed, the one or more of the loads may be removed, changed, or released which may enable the fixation rod to move (e.g., rotate, shift, change location, change orientation, etc.) relative to the pedicle screw. Such movement may cause the portion of the spinal column to not be stabilized because the false torque and resulting movement of the fixation rod may enable the vertebral bodies to move relative to each other to each other or another portion of the spine. False torque can also occur with the use of conventional screws such as mono-axial, and poly-axial without extension towers in similar fashion as described above.

FIG. 1 is a conventional skeletal fixation assembly 100 (hereinafter, "conventional assembly 100") of a type known in the art. As shown in FIG. 1, conventional assembly 100 includes a pair of screw extension towers 110 (hereinafter together referred to as "towers 110" and each, a "tower 110"), a pair of pedicle screw bodies 115 (hereinafter together referred to as "bodies 115" and each, a "body 115"), and a conventional fixation rod 120.

Tower 110 may include a rigid generally cylindrical member that includes a first end that is removably attached to body 115 and a second, opposite end that can be gripped or positioned by a medical practitioner (e.g., doctor, surgeon, nurse, etc.) to move and/or align body 115 during a medical procedure in which conventional assembly 100 is attached to vertebral bodies (e.g., shown as vertebrae 1 and vertebrae 2) included in a spinal column of a patient. The first end may include a frangible mechanism that allows tower 110 to be detached from body 115 by the medical practitioner. Body 115 may be made of a rigid U-shaped material to which tower 110 is removably attached (e.g., to the end corresponding to the open or top end of the "U"). Body 115 may also include a pedicle screw (not shown in FIG. 1) that protrudes through an opening (e.g., in the end corresponding to the closed or bottom end of the "U") that can be installed and/or screwed into a vertebrae. Body 115 also includes one or more set screws (not shown in FIG. 1) that can be used to fasten conventional fixation rod 120 to body 115. Conventional fixation rod 120 may include a rod made of a rigid material (e.g., a metal or metal allow, composite, ceramic, hard plastic, etc.) that can be inserted into and/or fastened to body 115 (e.g., using the setting screw). Conventional fixation rod 120 may include a predetermined bend radius or arc (hereinafter, a "medical curvature") based on a medical diagnosis or procedure performed by the medical practitioner to control the manner in which the vertebral bodies are to be stabilized.

When conventional fixation rod 120 is inserted in and fastened to bodies 115 (e.g., by tightening each setting screw to a predetermined torque setting), the first ends of towers 110 may move as the setting screws are tightened causing the first ends of towers 110 to make contact and/or interfere with each other when the bend radius or arc of conventional fixation rod 120 is less than a threshold. Such interference may preclude towers 110 and bodies 115 from assuming a predetermined position or orientation, which may impart certain induced loads on conventional fixation rod 120. The induced loads may cause a false torque condition to exist with respect to conventional assembly 100. Furthermore, the interference may also, or alternatively, cause conventional fixation rod 120 to rotate or change position when the setting screws are tightened which may cause the medical practitioner to loosen the setting screws, reposition conventional fixation rod 120 to the desired position or orientation, and attempt to retighten the setting screws. When towers 110 are removed and/or disconnected from bodies 115 (e.g., as called for by the medical procedure), the false torque condition may enable bodies 115 and/or conventional fixation rod 120 to change position or orientation thus precluding the vertebral bodies from being stabilized or causing the vertebral bodies to be stabilized in a manner that is not intended by the medical practitioner.

DESCRIPTION OF THE DRAWINGS

FIGS. 2A and 2B are diagrams of the conventional skeletal fixation assembly of FIG. 1 and an example skeletal fixation assembly, in which the systems and/or methods described herein may be implemented, respectively;

FIG. 3A and FIG. 3B are diagrams of an example a fixation rod of FIG. 2B;

FIG. 4A is a diagram of example components of a conventional skeletal fixation assembly associated with a false torque condition;

FIG. 4B and FIG. 4C are diagrams of example components of a skeletal fixation assembly that precludes a false torque condition;

FIGS. 5A-5C are diagrams of example attachment segments of a fixation rod associated with different cross sections;

DETAILED DESCRIPTION

Figure 1:
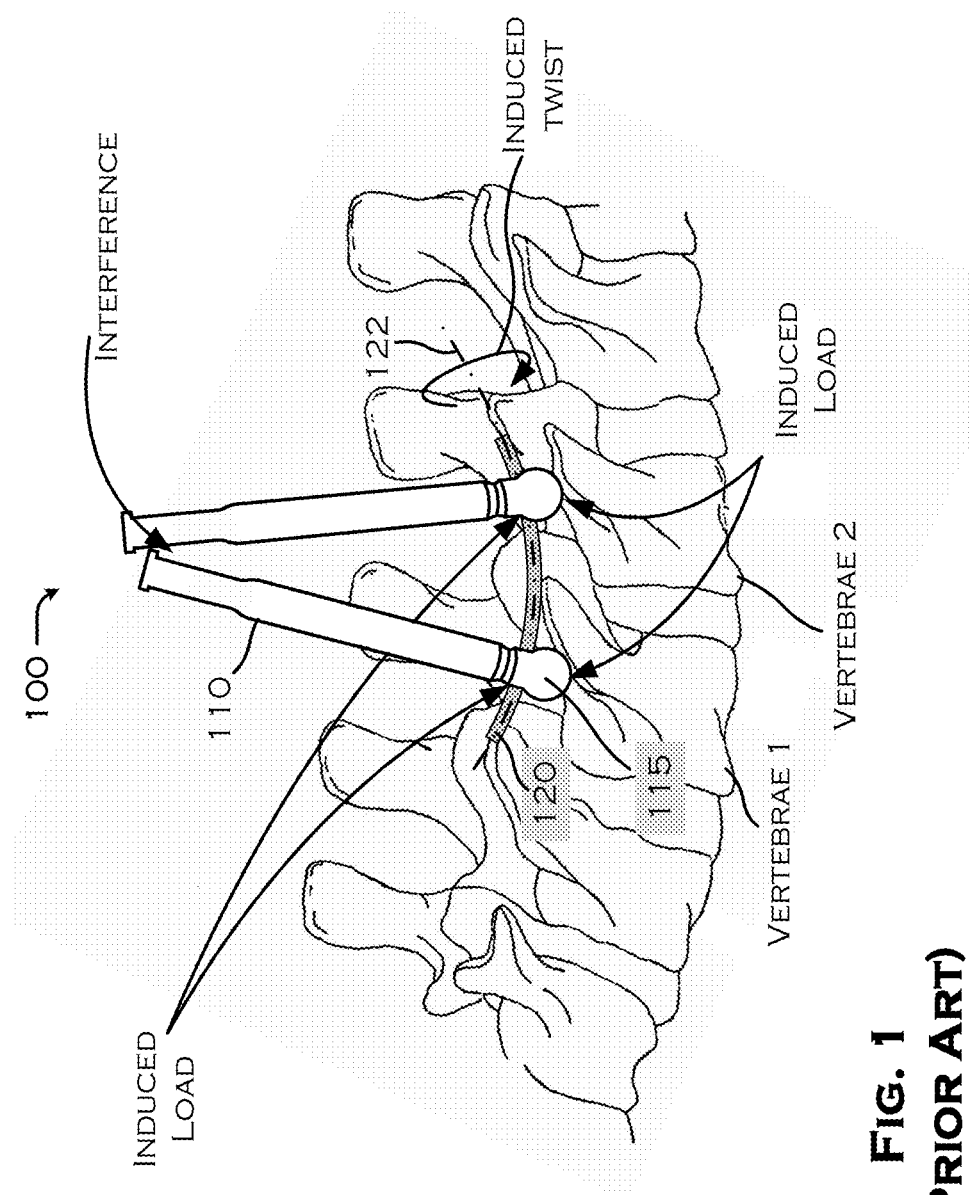
FIG. 1 is a diagram of a conventional skeletal fixation assembly.

The systems, methods, technologies, and/or techniques (hereinafter referred to as the "systems and/or methods"), described herein, may include a skeletal fixation assembly that is installed in the patient in a manner that precludes two or more screw extension towers, associated with the skeletal fixation assembly, from contacting and/or interfering with each other. Precluding the screw extension towers from making contact and/or interfering with each other may enable the skeletal fixation assembly to be installed on two or more vertebral bodies of a portion of a spinal column and/or two or more bones or bone fragments (e.g., in connection with a bone fracture) associated with the patient without creating a false torque condition. The installation of the skeletal fixation assembly without creating the false torque condition may ensure that the vertebral bodies, bones, and/or bone fragments remain in a fixed position and/or orientation relative to each other (hereinafter, "stabilized" or a "stabilized condition") after the extension towers are removed from the skeletal fixation assembly. Additionally, or alternatively, the installation of the skeletal fixation assembly without creating the false torque condition may preclude or reduce certain loads, unknown to and/or not intended or desired by the medical practitioner, from being imparted to the vertebral bodies, bones, and/or bone fragments, and/or pedicle screws associated with the skeletal fixation assembly. The term patient, as used herein, may include any human subject or animal subject having a skeletal structure.

The systems and/or methods may include a fixation rod that includes a first bend radius or arc and one or more second bend radii or arcs. The first bend radius or arc may, for example, correspond a predetermined medical curvature based on a medical diagnosis or procedure performed by a medical practitioner to ensure that that vertebral bodies of a spinal column and/or bone fragments of a fracture bone associated with a patient are stabilized. Additionally, or alternatively, the one or more second bend radii or arcs (hereinafter collectively referred to as "local curvatures" and each, a "local curvature") may be determined to ensure that two or more screw extension towers, associated with the skeletal fixation assembly, do not make contact or interfere with each other when bodies, to which the screw extension towers are attached, are fastened to the fixation rod. The local curvatures may be created at one or more locations of the fixation rod in a manner that preserves and/or does not change or affect the medical curvature of the fixation rod. The systems and/or methods may also, or alternatively increase an axial range of motion that the pedical screws are free to move or pivot that enables improved and or easier fixation in spines or bone fractures of patients with severe and/or complicated curves (e.g., in one or more of the coronal plane, sagittal plane, or transverse plane). Such improved and/or easier fixation may occur by enabling the pedical screw bodies (to which the pedical screws are pivotally attached) to engage or attach to the fixation rod at one or more fixation points in a shorter interval that would otherwise be possible. While the description below describes the systems and methods in the context of stabilizing a patients vertebral bodies, in an additional or alternatively implementation, the systems and/or methods may not be so limited. The systems and/or methods may, for example, be described in the context of other bones and/or bone fragments associated with a patient such as stabilizing a first bone fragment and a second bond fragment associated with a fractured bone within a patient.

The systems and/or methods may enable a cross sectional area of a fixation rod to be created or modified to preclude the fixation rod from rotating when being fastened to a body associated with a skeletal fixation assembly. Precluding the rotation of the fixation rod may eliminate the likelihood of a false torque condition being created and/or may preclude or reduce certain loads, unknown to and not intended or desired by the medical practitioner, from being imparted to the vertebral bodes and/or pedicle screws associated with the skeletal fixation assembly. Additionally, or alternatively, the cross sectional area of the fixation rod may be created or modified at a location that corresponds to a local curvature of the fixation rod and/or at a location on the fixation rod at which the body, associated with the skeletal fixation assembly, is fastened. The cross sectional area may also, or alternatively, be rotated or clocked about a longitudinal axis of the fixation rod to ensure that a screw extension tower does not make contact or interfere with another screw extension tower associated with the skeletal fixation assembly.

FIGS. 2A and 2B are diagrams of conventional assembly 100 of FIG. 1 that is known in the art and an example skeletal fixation assembly 200 (hereinafter "assembly 200") in which the systems and/or methods described herein may be implemented, respectively. As shown in FIG. 2A, conventional assembly 100 may include components 110-120 in a manner similar that that described above with respect to FIG. 1, as well as a pair of pedicle screws 130 (hereinafter collectively referred to as "screws 130" and each, a "screw 130"). Screw 130 may be rotatably attached to body 115 to permit screw 130 to freely rotate during installation in bone tissue of a vertebral body associated with a patient and/or to permit body 115 and/or tower 110 to swivel about screw 130 during installation of conventional assembly 100.

Conventional fixation rod 120 may be associated with a medical curvature 122 that is predetermined based on a medical diagnosis from a medical practitioner. Each screw 130 may be associated with a longitudinal axis (e.g., labeled "Screw Axis" in FIG. 2A) that intersects conventional fixation rod 120 at or in proximity to a location on conventional fixation rod 120 at which body 115 is fastened. Each tower 110 may be associated with a longitudinal axis (hereinafter referred to as "tower axis 112") (e.g., tower axis 112-1 for left tower 110 and tower axis 112-2 for right tower 110). A first screw axis, associated with left-most screw 130, may intersect tower axis 112-1 to form angle 155-1 and a second screw axis, associated with right-most screw 130, may intersect tower axis 112-2 to form angle 155-2. In one example, conventional fixation rod 120 may cause angle 155-1 and/or angle 155-2 to be greater than a first threshold and/or a combination of angle 155-1 and 155-2 (e.g., a sum, an average, etc.) be greater than a second, different threshold, which may cause left-most tower 110 and right-most tower 110 to make contact and/or to interfere with each other. The contact and/or interference may cause a false torque condition to exist.

As shown in FIG. 2B, assembly 200 may include towers 110, bodies 115, and screws 130, as well as fixation rod 220. The number of components, illustrated in FIG. 2B, is provided for explanatory purposes only. In practice, there may be additional components, fewer components, different components, or differently arranged components than illustrated in FIG. 2B. Also, in some implementations, one or more of the components of assembly 200 may perform one or more functions described as being performed by another one or more of the components of assembly 200.

Fixation rod 220 may be made of a material (e.g., a metal or metal alloy, composite, ceramic, hard plastic, etc.) of sufficient strength and/or rigidity to stabilize a patient's spine with assembly 200 is installed in the patient. Fixation rod 220 may also, or alternatively, include a medical curvature 222 and one or more local curvatures associated with one or more portions of fixation rod 220 to which bodies 115 are fastened. Medical curvature 222 may be predetermined by a medical practitioner based on a medical diagnosis or determined during the procedure performed by the medical practitioner.

A local curvature, to be described in greater detail below with respect to FIGS. 3A and 3B, may enable body 115 to be immovably fastened to fixation rod 220 in a manner that causes a screw axis, associated with body 115, to align with a tower axis associated with tower 110 to which body 115 is attached. For example, when the first screw axis, associated with left-most screw 130, aligns with tower axis 112-1, angle 155-1 may be less than the first threshold. In one example, first screw axis and tower axis 112-1 may align such that angle 155-1 is approximately zero. Additionally, or alternatively, when the first and second screw axes, associated with left-most and right-most screws 130, respectively, align with tower axes 112-1 and 112-2, respectively, a combination of angles 155-1 and 155-2 (e.g., a sum, an average, etc.) may be less than the second threshold. In one example, first screw axis and tower axis 112-1 may align and second screw axis and tower axis 112-2 may align such that a combination of angles 155-1 and 155-2 is approximately zero.

FIG. 3A and FIG. 3B are diagrams of an example fixation rod 220. As shown in FIGS. 3A and 3B, fixation rod 220 may include medical curvature 222 in a manner similar to that described above with respect to FIG. 2B, as well as a group of local curvatures 305-1, 305-2 and 305-3 (hereinafter together referred to as "local curvatures 305" and each, a "local curvature 305"). Fixation rod 220 is described below as including a single medical curvature 222 and a group of local curvatures 305 for explanatory purposes. Additionally, or alternatively, fixation rod 220 may include fewer local curvatures 305, additional medical curvatures 222 and/or local curvatures 305, different medical curvatures 222 and/or local curvatures 305, or differently arranged medical curvatures 222 and/or local curvatures 305. While FIGS. 3A and 3B describe medical curvature 222 and local curvatures 305 in a single two-dimensional plane for explanatory purposes, additionally, or alternatively, medical curvature 222 and/or local curvature 305 may exist as complex a curvature in three dimensions based on two or more orthogonal two-dimensional planes (e.g., two or more of the coronal (or frontal) plane, sagittal (median) plane, transverse (or horizontal) plane, and/or some other two dimensional plane).

Local curvature 305 may include a portion of fixation rod 220 associated with a contour or shape that does not conform to medical curvature 222 and/or which enables body 115 to be fastened to the portion of fixation rod 220 without causing a false torque condition. For example, local curvature 305-1 may include a first contour or shape that enables a first body 115 to be immovably fastened to a first portion of fixation rod 220, associated with local curvature 305-1, in a manner that causes a first screw axis, associated with first body 115, to align with a first tower axis 112 of a first tower 110 to which first body 115 is attached. Additionally, or alternatively, local curvature 305-2 may include a second contour or shape that enables a second body 115 to be immovably fastened to a second portion of fixation rod 220, associated with local curvature 305-2, in a manner that causes a second screw axis, associated with second body 115, to align with a second tower axis 112 of a second tower 110 to which second body 115 is attached. Local curvature 305-3 may include a third contour or shape that enables a third body 115 to be immovably fastened to a third portion of fixation rod 220, associated with local curvature 305-3, in a manner that causes a third screw axis, associated with third body 115, to align with a third tower axis 112 of a third tower 110 to which third body 115 is attached.

A combination of the first shape and/or contour, the second shape and/or contour, and/or the third shape and/or contour (e.g., associated with local curvatures 305-1, 305-2, 305-3, respectively and/or other shapes and/or contour associated with fixation rod 220) may be created in a manner that preserves medical curvature 222 associated with fixation rod 220. Such combination of shapes and/or countours may, for example, include an average, median, mean, etc. of a respective radii of curvature (e.g., shown as r1 and r2 for the first two curvatures of FIG. 3A) and/or arc length (e.g., shown as θ1 and θ2 for the first two curvatures of FIG. 3A) for each curvature or bend of fixation rode 220 and/or a combination of shapes and/or contours associated with sinusoidal, polynomial, parabolic, hyperbolic, elliptical, and/or other shapes and/or contours. Additionally, or alternatively, fixation rod 220 may include one or more local curvatures 305 in a manner that enables medical curvature 222 of fixation rod 220 to be approximately equal to medical curvature 122 of conventional fixation rod 120 (e.g., shown as a dashed line in FIG. 3A).

As shown in FIG. 3B, fixation rod 220 may include a group of attachment segments 310-1, 310-2 and 310-3 (hereinafter together referred to as "attachment segments 310" and each, a "attachment segment 310") that correspond to local curvatures 305-1, 305-2 and 305-3, respectively. Attachment segment 310 may include a portion of fixation rod 220 to which body 115 is immovably attached (e.g., body 115 is precluded from moving relative to attachment segment 310). Attachment segment 310 may also, or alternatively, include a length that is centered about a screw axis associated with body 115. In one example, attachment segment 310-1 may correspond to a generally straight portion of fixation rod 220 of sufficient length (e.g., shown as the shaded area of local curvature 305-1) to accommodate a width of body 115 to be fastened to attachment segment 310-1. Additionally, or alternatively, some or all of the length of attachment segment 310-1 may include a longitudinal axis (e.g., shown as "Local Axis in FIG. 3B) that does not align with medical curvature 122 and/or 222. The longitudinal axis may also, or alternatively, be created in a manner that enables body 115 to be attached to attachment segment 310-1 such that a screw axis, associated with body 115, aligns with tower axis 112 associated with tower 110 to which body 115 is attached. In one example, the local axis may be approximately perpendicular to the screw axis and/or tower axis 112. Fixation rod 220 may include one or more other local curvatures 305 (e.g., local curvature 305-2, 305-3, etc.) and/or one or more other attachment segments 310 (e.g., attachment segment 310-2, 310-3, etc.) to which one or more other bodies 115 are to be attached in a manner similar to that described above. Additionally, or alternatively, a first local axis, associated with attachment segment 310-1, may, for example, approximately align with a second local axis associated with attachment segment 310-2 and/or a third local axis associated with attachment segment 310-3. The approximate alignment of the first local axis, second local axis, and/or third local axis may cause tower 110-1 removably attached to a first body 115 to be approximately parallel to tower 110-2 and/or tower 110-3 removably attached to a second body 115 and/or third body 115, respectively, when first body 115, second body 115, and/or third body 115 are attached to attachment segment 310-1, 310-2 and/or 310-3, respectively. The approximately parallel towers 110 may preclude tower 110-1, tower 110-2, and/or tower 110-3 from making contact with each other.

FIG. 4A is a diagram of an example portion of conventional assembly 100 (hereinafter "conventional assembly portion 400") associated with a false torque condition. As shown in FIG. 4A, conventional assembly portion 400 may include components 110 through 130 as described above with respect to FIG. 2A. Additionally, body 115, associated with conventional assembly portion 400, may include a set screw 405 and a fixation rod saddle 410. Set screw 405 may be made of a rigid material (e.g., metal, plastic, ceramic, etc.) that includes threads that enable a medical practitioner to tighten set screw 405 against conventional fixation rod 120 (as shown by the downward pointing arrow and clockwise-pointing dashed arrow in FIG. 4A). Saddle 410 may be made of a rigid material and may include a shape that permits conventional fixation rod 120 to be seated and held in place when set screw 405 is tightened (e.g., as shown in the detailed figures of set screw 405). In one example, set screw 405 may be tightened to a predetermined setting (e.g., torque setting, a force setting, etc.), which may cause body 115 to be fastened to conventional fixation rod 120. When tower 110 interferes with another tower 110, associated with conventional assembly 100, a false torque condition may be created (e.g., shown by the dashed curved arrow labeled False Torque Condition in FIG. 4A) in a manner similar to that described above with respect to FIG. 1, when set screw 405 is not flush against conventional fixation rod 120. Additionally, or alternatively, when set screw 405 is tightened, fixation rod 120 may not seat properly within saddle 410, which may cause saddle 410 and/or screw 130 (e.g., including an approximately spherical head of screw 130) to become impinged between and/or make contact with body 115 and/or conventional fixation rod 120 (e.g., shown as the dashed straight arrow labeled "False Torque Condition"). Such impingement and/or contact may impart unwanted or unknown loads into the vertebral bodies and/or bone fragments of a patient and/or may reduce the range in which body 115, saddle 410 or tower 110 is free to move and/or pivot relative to screw 130. When the medical practitioner removes tower 110 from body 115, the interference with the other tower 110 may be removed, and body 115 may be free to rotate (e.g., as shown by the clockwise-pointing solid arrow in FIG. 4A). When body 115 rotates, conventional fixation rod 120 may not be seated and/or held in place within saddle 410 and/or body 115 may not be fastened to conventional fixation rod 120. In this example, conventional fixation rod 120 may be free change location or orientation relative to body 115 and/or rotate about the medical curvature 122 which may not stabilize vertebral bodies and/or bone fragments associated with a patient.

Figure 4C:
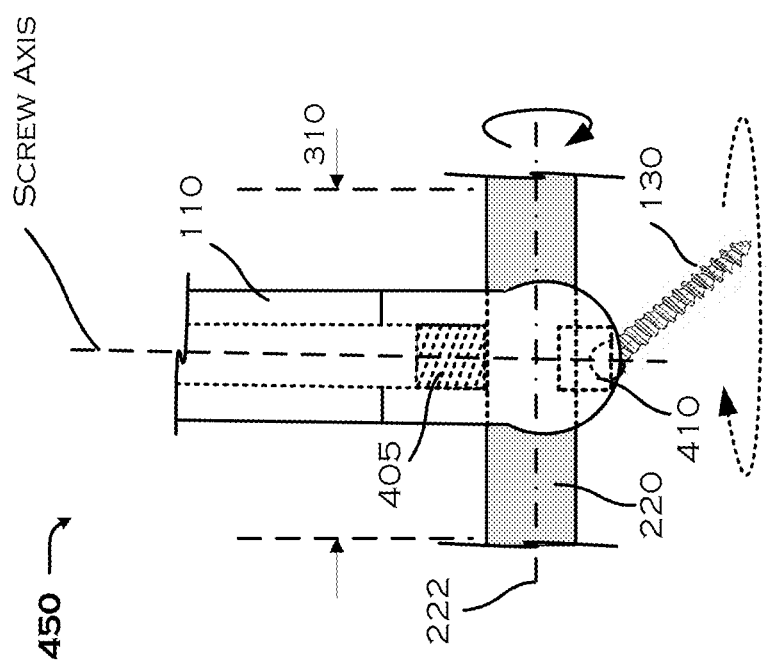

FIGS. 4B and 4C are diagrams of an example portion of assembly 200 (hereinafter "assembly portion 450") that precludes a false torque condition from occurring. As shown in FIG. 4B, assembly portion 450 may include fixation components tower 110, body 115, screw 130, and fixation rod 220 as described above with respect to FIG. 2B. Assembly portion 450 may also include set screw 405 and saddle 410 as described in FIG. 4A. Fixation rod 220 may include attachment segment 310 to which body 115 is immovably attached when set screw 405 is tightened against fixation rod 220 causing fixation rod 220 to be seated and/or held in place within saddle 410. In this example, a false torque condition may not exist because tower 110 does not interfere with another tower 110 associated with assembly 220 and/or because screw 130 is not impinged between and/or does not make contact with fixation rod 220 and/or body 115. In one example, fixation rod 220 may include a cross section that is of a particular shape (e.g., circular, elliptical, etc.) that permits to fixation rod 220 to rotate relative to body 115 in the event that set screw 405 is not tightened to the predetermined setting (e.g., a torque setting, a force setting, etc.) or loosens over time.

As shown in FIG. 4C, assembly portion 450 may include saddle 410 that permits screw 130 to freely swivel or pivot axially about the screw axis (as shown by the dashed curved arrow in FIG. 4C). Such freedom to axially pivot may enable screw 115 to be installed in the vertebral bodies or bone fragments at a variety of angles without causing a false torque condition in the patient. Additionally, or alternatively, the freedom of screw 115 to axially pivot may allow greater flexibility to install assembly portion 450 in the patient based on the geometry of the vertebral bodies, bone fragments, or orientation or shape of fixation rod 220.

Figure 5C:
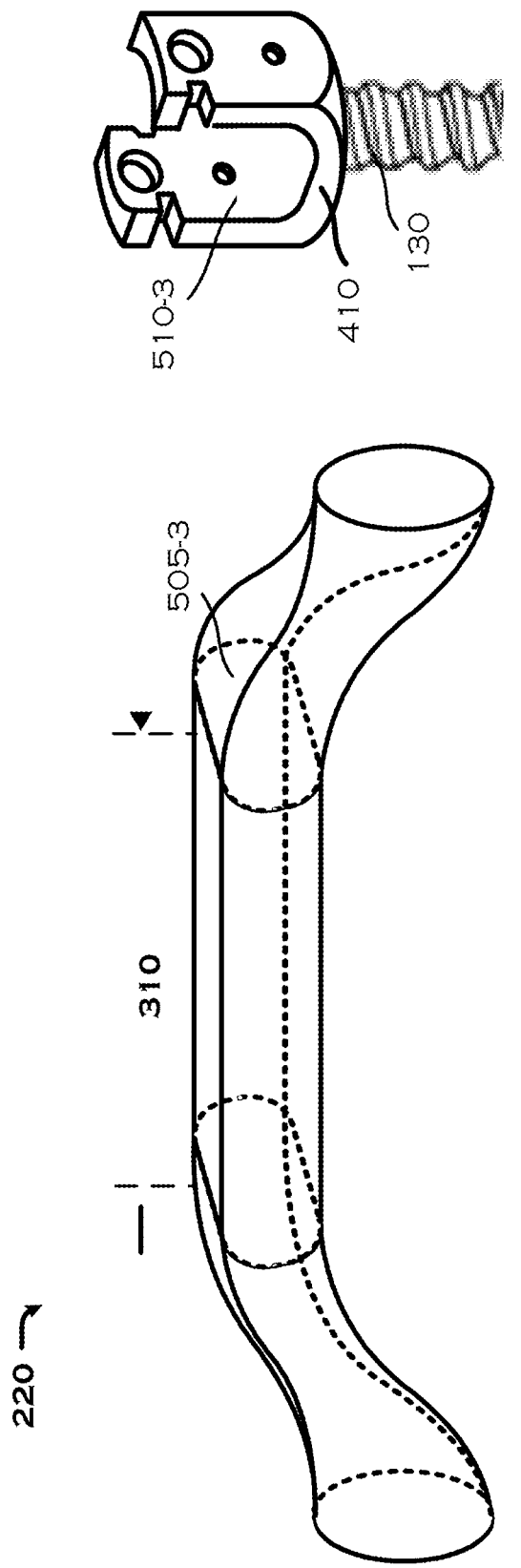

FIGS. 5A-5C are diagrams of example attachment segments 310 of fixation rod 220 associated with different cross section. As illustrated in FIGS. 5A-5C, fixation rod 220 may include attachment segment 310 associated with a cross section 505. In one example, a first cross sectional area 505 may correspond to a circular cross sectional area 505-1 as shown in FIG. 5A. Saddle 410, associated with body 115, may include an aperture 510 into which fixation rod 220 is inserted and can be seated and/or held in place when set screw 405 (not shown in FIG. 5A) is tightened against fixation rod 220 to fasten fixation rod 220 to body 115. In one example, a first aperture 510 may correspond to a circular aperture 510-1 (e.g., as shown in FIG. 5A) that may enable saddle 410 to receive fixation rod 220, associated with circular cross sectional area 505-1. The insertion of fixation rod 220, associated with circular cross section 505-1, into circular aperture 510-1, associated with saddle 410, may enable fixation rod 220 to be seated and/or held in place within saddle 410 and/or body 115.

Additionally, or alternatively, as illustrated in FIG. 5B, a second cross sectional area 505 may correspond to a hexagonal cross sectional area 505-2. A second aperture 510 may also, or alternatively, correspond to a hexagonal aperture 510-2 (e.g., as shown in FIG. 5B) that may enable saddle 410 to receive fixation rod 220, associated with hexagonal cross sectional area 505-2. The insertion of fixation rod 220, associated with hexagonal cross section 505-2, into hexagonal aperture 510-2, associated with saddle 410, may enable fixation rod 220 to be seated and/or held in place within saddle 410 and/or body 115. Additionally, or alternatively, the combination of hexagonal cross section 505-2 and hexagonal aperture 510-2 may make fixation rod 220 more resistant to rotating or twisting within saddle 410 compared with fixation rod 220, associated with circular cross section 505-1, that is seated in saddle 405 associated with circular aperture 510-1.

Additionally, or alternatively, as illustrated in FIG. 5C, a third cross sectional area 505 may correspond to an oval cross section 505-3. A third aperture 510 may also, or alternatively, correspond to an oval aperture 510-3 (e.g., as shown in FIG. 5C) that may enable saddle 410 to receive fixation rod 220, associated with oval cross sectional area 505-3. The insertion of fixation rod 220, associated with oval cross section 505-3, into oval aperture 510-3, associated with saddle 410, may enable fixation rod 220 to be seated and/or held in place within saddle 410 and/or body 115. Additionally, or alternatively, the combination of oval cross section 505-3 and oval aperture 510-2 may make fixation rod 220 more resistant to rotating or twisting within saddle 410 compared with fixation rod 220, associated with circular cross section 505-1, that is seated in saddle 405 associated with circular aperture 510-1.

In the discussion above, cross sectional area 505 and/or aperture 510 are described with respect to a circular, an oval, or a hexagonal shape for explanatory reasons. Additionally, or alternatively cross sectional area 505 and/or aperture 510 may include other cross sections and/or shapes such as, for example, an elliptical shape, a square shape, a rectangular shape, a triangular shape, pentagonal shape, etc.

Figure 6:
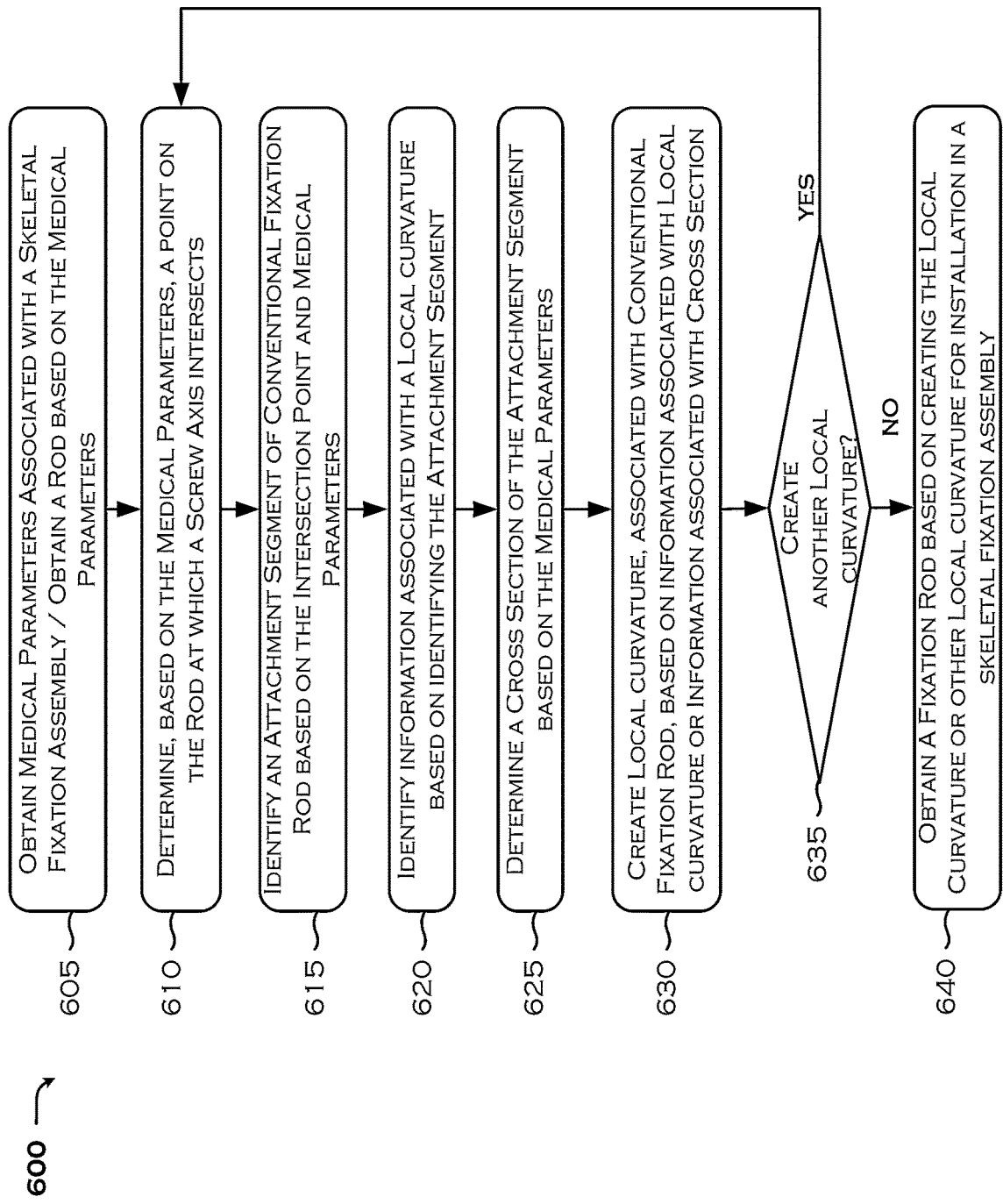
FIG. 6 is a flow chart of an example process for creating a fixation rod for use in a skeletal fixation assembly.

FIG. 6 is a flow chart of an example process 600 for creating a fixation rod 220 for use in assembly 200. Process 600 may be performed by a medical practitioner while installing assembly 200 in a spinal column associated with a patient. Additionally, or alternatively, some or all of process 600 may be performed by device and/or or collection of devices separate from, or in combination with, assembly 200. FIGS. 7A-7E are diagrams of example stages of formation 700-790 (hereinafter referred to collectively as "stages 700-790" and individually, as "stage 700," "stage 725," "stage 750," "stage 775," or "stage 790"), respectively, of fixation rod 220 associated with assembly 200. Some or all of process 600 of FIG. 6 will be described with references to some or all stages 700-790 of FIGS. 7A-7E, respectively.

Assume that a medical practitioner performs a medical procedure on a patient and determines that a portion of the spinal column of the patent is to be stabilized skeletal fixation assembly (e.g., assembly 200 of FIG. 2B). Assume further that the medical practitioner specifies information and/or parameters associated with assembly 200 to be used to stabilize the portion of the spinal column (hereinafter referred to as "medical parameters"). For example, the medical parameters may include information that identifies a length and/or a medical curvature 122, associated with conventional fixation rod 120, to be used to stabilize two or more vertebral bodies of the spinal column; information identifying one or more locations on each of the vertebral bodies at which a respective pedicle screw (e.g., screw 130) can be inserted; information identifying a width of body 115 to be used to fasten fixation rod 220; information that specifies a cross section (e.g., a shape, cross sectional area, radius, diameter, etc.) of attachment segment 310 of fixation rod 220; information specifying an aperture of saddle 410 (e.g., a shape, cross sectional area, radius, diameter, etc.) associated with body 115; etc. The medical practitioner may, in one example, enter the parameters into a user interface displayed by a user device and the user device may receive the parameters and may store the parameters in a memory associated with the user device.

As shown in FIG. 6, process 600 may include obtaining medical parameters associated with a skeletal fixation assembly and obtaining a rod based on the medical parameters (block 605), and determining, based on the parameters, a point on the rod at which a screw axis intersects the rod (block 610). For example, a medical practitioner may obtain predetermined parameters, associated with assembly 200, and may, based on the parameters, identify a location on a vertebral body in which screw 130 is to be inserted. Additionally, or alternatively, the medical practitioner may identify a longitudinal axis, associated with screw 130 (e.g., hereinafter referred to as "screw axis"), when screw 130 is installed in the vertebral body. The medical practitioner may also, or alternatively, use one or more known methods to obtain a rod (e.g., conventional fixation rod 120 or some other rod) that corresponds to the length and/or medical curvature 122 specified by the medical parameters. The medical practitioner may determine a location on conventional fixation rod 120 at which the screw axis intersects conventional fixation rod 120 (hereinafter the "intersection point"). The intersection point may be based on a location and/or orientation of conventional fixation rod 120, relative to the location on the vertebral body in which screw 130 is to be inserted, in the event that conventional assembly 100 is attached to the patient.

Additionally, or alternatively, the steps performed by the medical practitioner could be performed automatically by a computing device executing logic and/or a set of instructions stored in a memory. For example, the medical practitioner may instruct the computing device to obtain the medical parameters (e.g., using a pointing device such as a mouse, by pressing one or more buttons on a keyboard, etc.) and the computing device may, based on the instruction, retrieve the parameters from the memory. Additionally, or alternatively, the computing device may identify the location on the vertebral body in which screw 130 is to be inserted based on the parameters. The computing device may also, or alternatively, determine an orientation of screw 130 when inserted in the vertebral body, may identify the screw axis based on the orientation of screw 130, and may determine the intersection point of conventional fixation rod 120.

Additionally, or alternatively, an axis that is different than the screw axis may be used to determine the intersection point, such as when screw 130 is inserted in the vertebral body and/or bone fragment on an axis that deviates from a vertical axis at an angle that is greater than a particular threshold (e.g., 20 degrees, 25 degrees, 30 degrees, 35 degrees, 40 degrees, etc.). In this example, the axis may be substantially vertical or parallel to the coronal plane as would be understood by a person skilled in the art and may intersect a location at which screw 130 is inserted into the vertebral body or bone fragment.

Figure 7A:
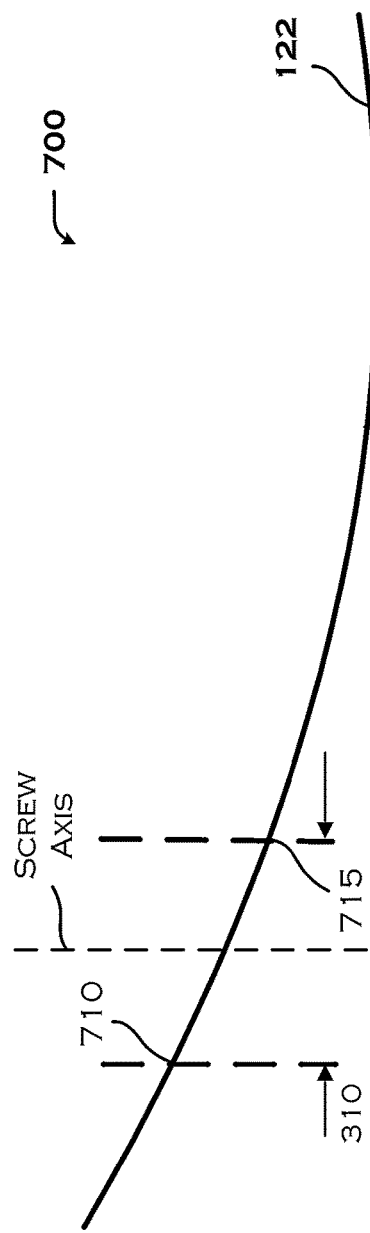
FIGS. 7A-7E are diagrams of example stages of formation of a fixation rod associated with a skeletal fixation assembly.

As also shown in FIG. 6, process 600 may include identifying an attachment segment of the conventional fixation rod based on the intersection point and the medical parameters (block 615). For example, the medical practitioner may determine a first point and a second point located on conventional fixation rod 120 based on the intersection point of the screw axis and a width of body 115 or some other distance obtained from the medical parameters. As shown in FIG. 7A, stage 700 may include conventional fixation rod 120 associated with medical curvature 122 and may identify a first point 710 and a second point 715 located on conventional fixation rod 120. In one example, first point 710 and second point 715 may be approximately equal distance from the intersection point of the screw axis with conventional fixation rod 120. In another example, first point 710 and second point 715 may not be approximately equal distance from the intersection point. The distance between first point 710 and/or second point 715 may be based on a width of body 115 and/or some other distance obtained from the medical parameters (e.g., a predetermined distance, a predetermined percentage of the length of conventional fixation rod 120, etc.).

Additionally, or alternatively, the user device may automatically determine a location associated with first point 710, a location associated with second point 715, and/or the distance between first point 710 and second point 715 based on the intersection point of the screw axis and the width of body 115 and/or some other distance obtained from the medical parameters.

As further shown in FIG. 6, process 600 may include identifying information associated with a local curvature based on identifying the attachment segment (block 620).

For example, the medical practitioner may determine a first local axis, associated with first point 710 and second point 715, that enables attachment segment 310 to be created to which body 115 can be attached in a manner that precludes tower 110 (e.g., attached to body 115) from making contact with and/or interfering with another tower 110 associated with assembly 200. In one example, the first local axis may be determined in a manner that is approximately perpendicular to the screw axis and/or that causes the screw axis to be aligned with tower axis 112 associated with tower 110. Additionally, or alternatively, the first local axis may be determined in a manner that causes a first angle (e.g., angle 155-1 of FIG. 2B) between tower axis 112 to be less than a first threshold (e.g., as described above with respect to FIG. 2B). Additionally, or alternatively, the first local axis may be determined in a manner that causes a combination (e.g., a sum, an average, etc.) of the first angle and a second angle (e.g., angle 155-2 of FIG. 2B) between a different screw axis and particular tower axis 112, of a different tower 110 associated with assembly 200, to be less than a second threshold.

Additionally, or alternatively, a user device may execute logic and/or one or more instructions stored in a memory to automatically determine the first local axis associated with first point 710 and second point 715 that enables attachment segment 310 to be created in a manner similar to that described above.

Figure 7B:
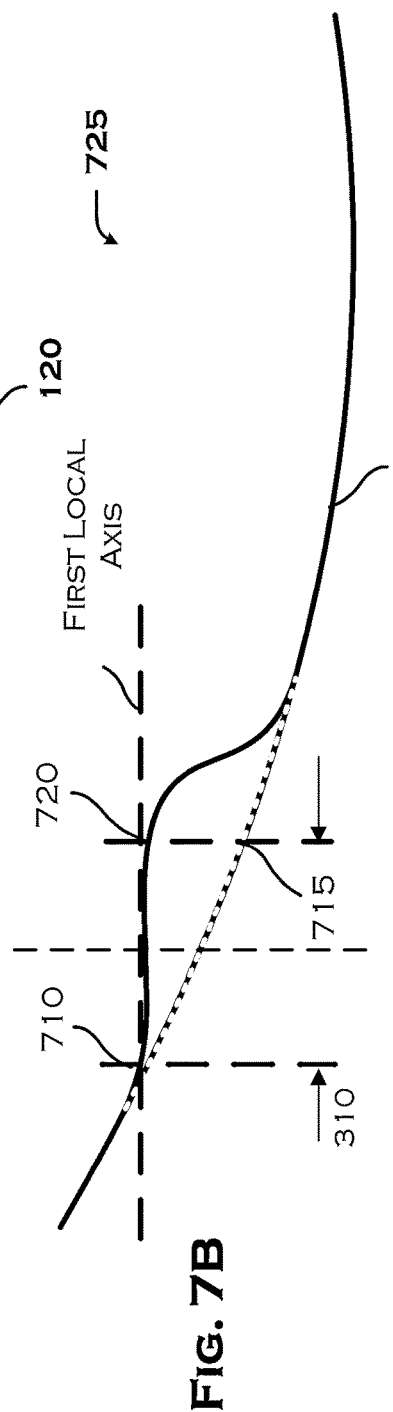

As shown in FIG. 7B, stage 725 may identify the first local axis, associated with first point 710 and second point 715, that is approximately perpendicular to the screw axis. The first local axis may, for example, intersect conventional fixation rod 120 at first point 710, but may not intersect conventional fixation rod 120 at second point 715. In this example, the first local axis may intersect a third point 720 that is not located on conventional fixation rod 120. Third point 720 may, for example, be located at an intersection of the first local axis and an axis, associated with second point 715, that is parallel to the screw axis. The first local axis may, therefore, intersect first point 710 that is located on conventional fixation rod 120 and third point 720 that is not located on conventional fixation rod 120. The first local axis may represent a longitudinal axis on which a local curvature 305 and/or attachment segment 310 may be created to form fixation rod 220 (e.g., as shown in stage 750 of FIG. 7C).

Figure 7C:
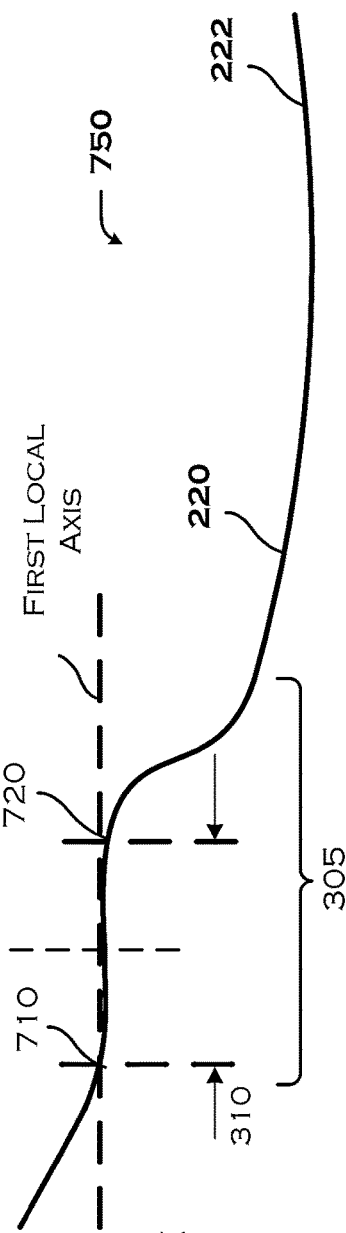

As shown in FIG. 7C, local curvature 305 and/or attachment segment 310 may be located at a distance that is closer to a center point, associated with a bend radii of medical curvature 122, than conventional fixture rod 120 (hereinafter, referred to as "concave local curvature 305" or "concave faster portion 310").

Figure 7D:
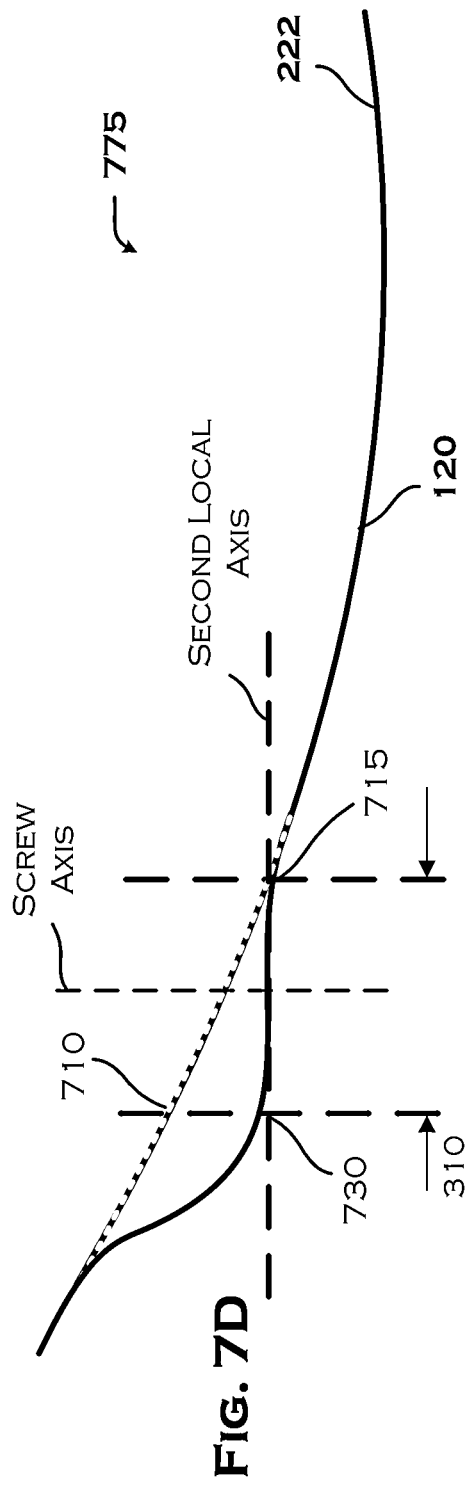

Additionally, or alternatively, as shown in stage 775 of FIG. 7D, a second local axis may be determined based on second point 715 that is located on conventional fixture rod 120 and a fourth point 730 that is not located on conventional fixation rod 120. Fourth point 730 may, for example, be located at the intersection of the second local axis and an axis, associated with first point 710, that is parallel to the screw axis. The second local axis, therefore, may intersect second point 715 that located on conventional fixation rod 120 and fourth point 730 that is not located on conventional fixation rod 120. The second local axis may represent a longitudinal axis on which attachment segment 310 may be created to form fixation rod 220 (e.g., as shown in stage 790 of FIG. 7E).

Figure 7E:
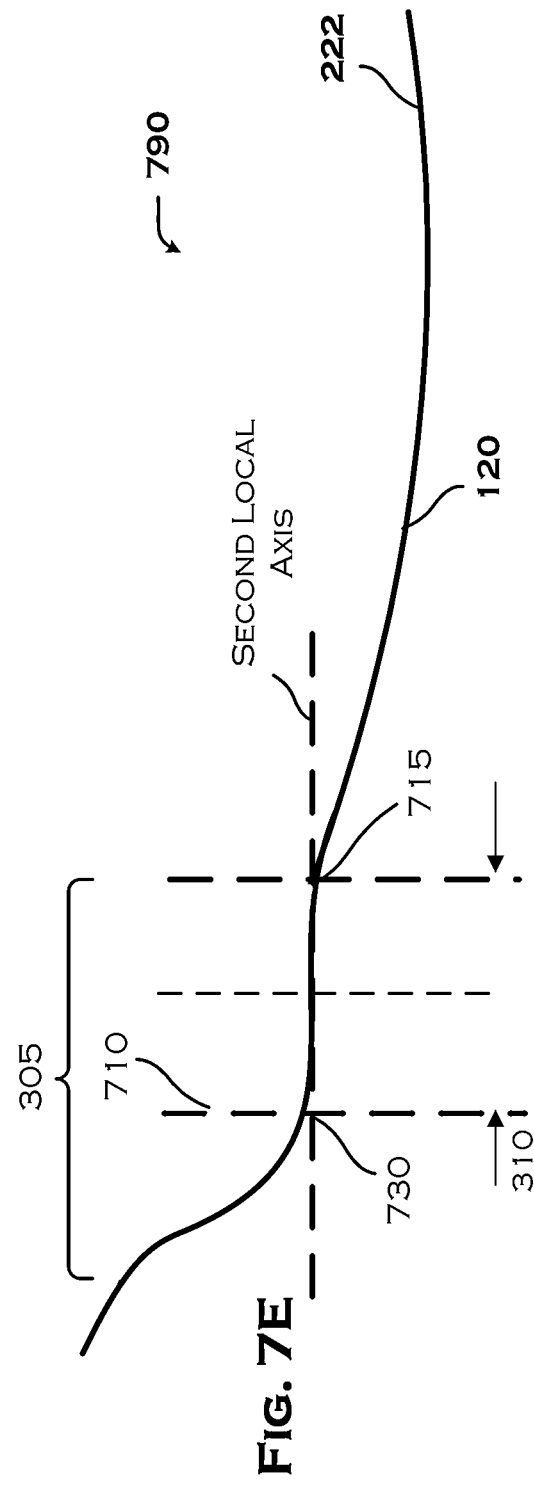

As shown in FIG. 7E, local curvature 305 and/or attachment segment 310 may be located at a distance that is further from a center point, associated with a bend radii of medical curvature 122, than conventional fixture rod 120 (hereinafter, referred to as "convex local curvature 305" or "convex faster portion 310").

The medical practitioner may also, or alternatively, record information associated with concave local curvature 305 and/or convex local curvature 305 that includes, for example, information identifying the intersection point, first point 710, second point 715, third point 720, fourth point 730, the first local axis, the second local axis curvature, etc.; and/or information associated with convex local curvature 305 including, for example, information identifying the intersection point, first point 710, second point 715, fourth point 730, the local axis, etc.

While the description above describes the determination of a concave and/or convex local curvature and/or attachment segment 310 in a two-dimensional plane (e.g., based on a coronal plane, the sagittal plane, transverse plane, or some other two-dimensional plane), the concave and/or convex local curvature 305 and/or attachment segment 310 may also, or alternatively and in a manner similar to that described above, be determined in a different two-dimensional plane; in three-dimensions that includes two or more two-dimensional planes (e.g., two or more of the coronal plane, sagittal plane, transverse plane, or some other two-dimensional plane); and/or based on another coordinate system (e.g., Cartesian coordinates, cylindrical coordinates, spherical coordinates, etc.).

As yet further shown in FIG. 6, process 600 may include determining a cross section of the attachment segment based on the medical parameters (block 625). For example, the medical practitioner may obtain, from the medical parameters, information associated with a cross section (e.g., a cross sectional shape, dimensions, etc.) of fixation rod 220 and/or attachment segment 310. Additionally, or alternatively, the medical practitioner may obtain, from the medical parameters, information associated with aperture 510 of saddle 410 within body 115 (e.g., information specifying a shape and/or dimension of aperture 510). Based on the information associated with aperture 510, the medical practitioner may determine a cross section and/or dimensions of fixation rod 220 and/or attachment segment 310.

Additionally, or alternatively, the medical practitioner may specify whether the cross section is to be clocked in a particular direction (e.g., clockwise, counter clockwise, etc. about a longitudinal axis associated with attachment segment 310) to ensure that towers 110 to not make contact or interfere when fastened to attachment segment 310.

As also shown in FIG. 6, process 600 may include creating a local curvature, associated with the conventional fixation rod, based on the information associated with the local curvature or information associated with the cross section (block 630). For example, the medical practitioner may identify a portion of conventional fixation 120 between first point 710 (FIG. 7A) and second point 715 (FIG. 7A) and may cause a longitudinal axis, associated with the identified portion of conventional fixation rod 120, to align with the first local axis to create concave local curvature 305 and/or attachment segment 310 (e.g., when a concave local curvature 305 and/or concave attachment segment 310 is specified by the medical parameters). Additionally, or alternatively, the medical practitioner may cause the longitudinal axis, associated with the identified portion of conventional fixation rod 120, to align with the second local axis to create convex local curvature 305 and/or concave attachment segment 310 (e.g., when a convex local curvature 305 and/or attachment segment 310 is specified by the medical parameters). The medical practitioner may also, or alternatively, cause a cross section of the attachment segment 310 (e.g., concave or convex) to change to a particular cross section specified in the medical parameters (e.g., a circular, elliptical, hexagonal, oval, pentagonal, octagonal, etc. cross section).

In one example, the creation of local curvature 305 and/or the change in cross section of attachment segment 310 may be created by the medical practitioner using a mechanical device to bend and/or reshape the identified portion of conventional fixation rod 120 and/or to change the cross section. Additionally, or alternatively, the medical practitioner may insert a conventional fixation rod 120 and/or some other rod into a device that may automatically create local curvature 305 and/or change the cross section of attachment segment 310. Additionally, or alternatively, fixation rod 220 may be manufactured in a manner that includes local curvature 305, the cross section specified by the medical parameters, or a medical bend 222 that conforms to conventional medical 122 specified by the medical parameters.

As also shown in FIG. 6, if another local curvature is to be created (block 635—YES), then process 600 may include determining, based on another point on the rod at which another screw axis intersects (block 610). For example, if another local bend 305 is to be incorporated into fixation rod 220, the medical practitioner may identify a different location on the vertebral body or another, different vertebral body at which a particular screw 130 is to be attached. Additionally, or alternatively, medical practitioner may, in a manner similar to that described above with respect to block 610, identify a particular screw axis, associated with particular screw 130, and a different location at which particular screw axis intersects fixation rod 220. Medical practitioner may also, or alternatively, cause other local bend 305 to be created and/or incorporated into fixation rod 220 in a manner similar to that described above with respect to blocks 615-630.

As further shown in FIG. 6, if another local curvature is not to be created (block 635—NO), then process 600 may include obtaining a fixation rod based on creating the local curvature or the other local curvature for installation in a skeletal fixation assembly (block 640). For example, another local curvature 305 is not to be incorporated into fixation rod 220, then medical practitioner may obtain fixation rod 220. The medical practitioner may also, or alternatively, use fixation rod 220 to stabilize the vertebral body and/or other vertebral body associated with a patient. In this example, the medical practitioner may install one or more screws 130 (e.g., screw 130, particular screw 130, etc.) into the vertebral body and/or the other vertebral body and may attach, to screws 130, assembly 200 that includes fixation rod 220. The medical practitioner may fasten one or more bodies 115 to fixation rod 220 in a manner that precludes one or more towers 110, to which bodies 115 are attached, from making contact and/or interfering with each other. Additionally, or alternatively, fixation rod 220 may prevent a torque condition from being created by precluding towers 110 from making contact and/or interfering with each other. The medical practitioner may also, or alternatively, detach towers 110 from bodies 115. After detaching towers 110, bodies 115 may remain fastened to fixation rod 220, which may preclude fixation rod 220 from changing a location and/or orientation, and/or from twisting or rotating relative to bodies 115. The same can hold true for conventional screws without towers attached.

The foregoing description provides illustration and description, but is not intended to be exhaustive or to limit the implementations to the precise form disclosed. Modifications and variations are possible in light of the above disclosure or may be acquired from practice of the embodiments.

For example, while a series of blocks have been described with regard to FIG. 6, the order of the blocks may be modified in other implementations. Further, non-dependent blocks may be performed in parallel.

It will be apparent that systems and methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" and "an" are intended to include one or more items and may be used interchangeably with "one" or "more." Where only one item is intended, the term "one" or similar language is used. Further, the phrase "based on" is intended to mean "based, at least in part, on" unless explicitly stated otherwise.

What is claimed is:

1. A skeletal fixation apparatus, comprising:
   two or more fixation rod receiving "U" shaped bodies that are attached to two or more screws that are adapted to be inserted into vertebral bodies associated with a patient, each screw having a screw axis;
   two or more cylindrical tower members that are attached to the two or more bodies to control the movement or alignment of the two or more bodies when the skeletal fixation apparatus is being installed in the patient, each tower member having a tower axis; and
   a fixation rod manufactured with a plurality of curvatures extending along a length of the fixation rod, said fixation rod of sufficient strength or rigidity to stabilize the patient's spine extending between adjacent screws of the two or more screws, said fixation rod being manufactured having a first bend radius or arc corresponding to a predetermined medical curvature extending along the length of the fixation rod and two or more second bend radii or arcs, each second bend radius or arc defining a local curvature, each local curvature having an attachment segment with a generally straight portion having a local axis that is parallel to each other local axis and approximately perpendicular with each respective screw axis, the first bend radius or arc being different than the two or more second bend radii or arcs, the fixation rod with the predetermined medical curvature being selected based on a medical diagnosis associated with stabilizing the two or more vertebral bodies, the local curvatures being at two or more locations on the fixation rod while preserving the medical curvature in relation to the two or more cylindrical tower members, the local curvature overlaying the medical curvature, and the local curvatures configured to immovably fasten the two or more bodies to the fixation rod and configured to preclude the two or more cylindrical tower members from contacting each other when the skeletal fixation apparatus is installed in the patient, and wherein when the body is immovably attached to the fixation rod, the screw axis associated with the body aligns with the tower axis associated with the tower to which the body is attached, such that the approximate alignment of each local axis causes the two or more cylindrical tower members to be approximately parallel.

2. The skeletal fixation apparatus of claim 1, where a first body, of the two or more bodies, is attached to a first portion of the fixation rod that corresponds to a first local curvature of the two or more local curvatures.

3. The skeletal fixation apparatus of claim 2, where a second body, of the two or more bodies, is attached to a second portion of the fixation rod that corresponds to a second local curvature of the two or more local curvatures.

4. The skeletal fixation apparatus of claim 1, where a first longitudinal axis, associated with a portion of the local curvature, intersects a second longitudinal axis, associated with a first cylindrical tower member of the two or more cylindrical tower members, in a manner that precludes the first cylindrical tower member from making contact with a second cylindrical tower member, of the two or more cylindrical tower members, when a first body, of the two or more bodies and to which the first cylindrical tower member is attached, is immovably fastened to the portion of the local curvature.

5. The skeletal fixation apparatus of claim 4, where the first longitudinal axis is approximately perpendicular to the second longitudinal axis when the first body is immovably fastened to the portion of the local curvature.

6. The skeletal fixation apparatus of claim 5, where the first longitudinal axis being approximately perpendicular to the second longitudinal axis when the first body is immovably fastened to the portion of the local curvature precludes a false torque condition from being created,
the false torque condition enabling the first body to move relative to at least one of the two or more vertebral bodies when the first cylindrical tower member is detached from the first body.

7. The skeletal fixation apparatus of claim 1, further comprising:
a first local curvature that is different than the medical curvature, the first local curvature enabling a first body, of the two or more bodies, to be immovably attached to the first local curvature, and
a second body, of the two or more bodies, to be immovably attached to a second local curvature, the second body being different than the first body.

8. The skeletal fixation apparatus of claim 7, where the first local curvature and the second local curvature are aligned to enable the first body and the second body to be immovably attached to the fixation rod in a manner that precludes a first cylindrical tower member, attached to the first body, from making contact with a second cylindrical tower member attached to the second body.

9. The skeletal fixation apparatus of claim 7, where the first local curvature is associated with a first plane within a three-dimensional space and the second local curvature is associated with a second plane within the three-dimensional space,
the first plane corresponding to one of a coronal plane, a sagittal plane, or a transverse plane, the second plane corresponding to a different one of the coronal plane, the sagittal plane, or the transverse plane.

10. The skeletal fixation apparatus of claim 1, where two or more of the local curvatures correspond to a complex curvature in three-dimensions, the complex curvature being associated with two or more of a coronal plane, a sagittal plane, or a transverse plane.

11. The skeletal fixation apparatus of claim 1, where at least one of the local curvatures is concave relative to the medical curvature.

12. The skeletal fixation apparatus of claim 1, where at least one of the local curvatures is convex relative to the medical curvature.

13. The apparatus of claim 1 where the patient corresponds to a human subject or an animal subject.

14. The skeletal fixation apparatus of claim 1, wherein the attachment segment of the fixation rod has a circular or elliptical cross-section allowing the fixation rod to rotate relative to the body when not tightened or fixed by a set screw.

15. The skeletal fixation apparatus of claim 1, wherein each body further comprises a saddle inside the "U" shaped body, the saddle having an aperture to receive the fixation rod while permitting the screw attached to body to freely swivel or pivot axially prior to being tightened.

16. The skeletal fixation apparatus of claim 1, wherein the fixation rod has a cross-section at the attachment segments that is hexagonal to resist rotation of the fixation rod.

17. The skeletal fixation apparatus of claim 1, wherein the fixation rod has a cross-section at the attachment segments that is oval to resist rotation of the fixation rod.

18. A skeletal fixation apparatus, comprising:
a fixation rod having a length, a general curvature along the entire length, and a plurality of attachment segments along the length and within the general curvature, wherein the attachment segments each have a longitudinal axis that does not align with the general curvature;
a plurality of receiving bodies, each receiving body capable of engaging the fixation rod at a respective attachment segment;
a plurality of bone screws, each bone screw having an axis along the screw length and capable of insertion through a respective receiving body; and
a plurality of tower members, each tower member having an axis along the tower member length and capable of releasable engagement with a respective receiving body;

wherein the longitudinal axis of each attachment segment is approximately perpendicular to each respective screw axis and tower member axis; and wherein each of the tower members are precluded from contacting each other by virtue of their engagement with each respective receiving body.

\* \* \* \* \*